United States Patent [19]

Stecker

[11] Patent Number: 4,841,973
[45] Date of Patent: Jun. 27, 1989

[54] ELECTRICAL STIMULATORS

[76] Inventor: Harold D. Stecker, 73 Hedgerow Dr., Morrisville, Pa. 19067

[21] Appl. No.: 99,159

[22] Filed: Sep. 21, 1987

[51] Int. Cl.⁴ .............................................. A61N 1/36
[52] U.S. Cl. ..................................... 128/421; 128/422
[58] Field of Search ................................ 128/421, 422

[56] References Cited

U.S. PATENT DOCUMENTS

| | | | |
|---|---|---|---|
| 2,622,601 | 12/1952 | Nemec | 128/422 |
| 3,055,372 | 9/1962 | Browner | 128/421 |
| 3,096,768 | 7/1963 | Griffith, Jr. | 128/422 |
| 3,646,940 | 3/1972 | Timm et al. | 128/421 |
| 4,023,574 | 5/1977 | Nemec | 128/422 |
| 4,071,033 | 1/1978 | Nawracaj et al. | 128/422 |
| 4,147,171 | 4/1979 | Greene et al. | 128/421 |
| 4,155,366 | 5/1979 | Di Mucci | 128/421 |
| 4,305,402 | 12/1981 | Katims | 128/421 |
| 4,340,063 | 7/1982 | Maurer | 128/421 |
| 4,401,121 | 8/1983 | Rodler | 128/422 |
| 4,408,609 | 10/1983 | Axelgaard | 128/421 |
| 4,453,548 | 6/1984 | Maurer et al. | 128/421 |
| 4,528,984 | 7/1985 | Morawetz et al. | 128/421 |
| 4,539,993 | 9/1985 | Stanton | 128/421 |
| 4,550,733 | 11/1985 | Liss et al. | 128/421 |
| 4,556,051 | 12/1985 | Maurer | 128/421 |
| 4,580,570 | 4/1986 | Sarrell et al. | 128/421 |
| 4,632,117 | 12/1986 | James | 128/421 |
| 4,690,146 | 9/1987 | Alon | 128/422 |
| 4,724,841 | 2/1988 | Kastrubin et al. | 128/421 |

FOREIGN PATENT DOCUMENTS

| | | | |
|---|---|---|---|
| 1242186A | 7/1986 | U.S.S.R. | 128/421 |
| 0000063 | 1/1987 | World Int. Prop. O. | 128/421 |

OTHER PUBLICATIONS

"Neuro-Electric Therapy, Enkephalin and Drug Addiction"; M. A. Patterson, Int. Review of Opium Studies-1977.

Primary Examiner—Leo P. Picard
Assistant Examiner—Jessica J. Harrison
Attorney, Agent, or Firm—Daniel E. Kramer

[57] ABSTRACT

A portable single or two channel, electrically energized device for applying a series of therapeutic pulse type electrical stimulations to a human body member including individual channel controls for pulse frequency, pulse width and pulse amplitude and circuitry therefore.

4 Claims, 3 Drawing Sheets

ELECTRICAL STIMULATORS

BACKGROUND

1. Field of the Invention

This invention is directed towards apparatus for use in the treatment of drug addiction. It is further directed toward electronic apparatus for drug addiction therapy. It is further directed toward electronic apparatus which imposes electrical potential to the skin of a patient. It is further directed toward such apparatus where the potential is applied as impulses having adjustable parameters of amplitude, duration and frequency. It is further directed to such apparatus having two individual channels, each channel individually adjustable for amplitude, duration and frequency. It is further directed to electronic circuitry for producing such high voltage pulses from low voltage sources. It is further directed toward the method of treating chemical addiction by the process of substituting electrical pulses for the chemical of addiction.

2. Prior Art

Although electro-shock therapy has been used for years, especially in the treatment of schizophrenia, the inventor does not consider this technique to constitute prior art because of the high level of voltages and currents employed because of the inherently destructive effect of the treatment on the patient.

The use of low level electric shocks for the purpose of inducing analgesia has been known since at least 1972.

Margaret A. Patterson, a British physician and surgeon, experimented with and reported success in the use of low level pulses of direct current applied to electrodes positioned behind each ear. She employed a transistorized machine to apply square wave pulses having a duration of 0.25 milliseconds over the frequency range of 30 to 2,000 hertz. Reference is made to a book entitled "International Review of Opium Studies—1977" published by the University City Science Center, 3401 Market Street, Phila., PA, 19104 and to a Pharmakon/Patterson electric stimulator manufactured by European Electronic Systems Limited, Unit 3, West Station Industrial Estate, Maldon, Essex, England.

BRIEF DESCRIPTION OF THE INVENTION

This invention is directed toward apparatus for use in reducing the pain and discomfort arising from withdrawal of a substance or activity on which the body has become psychologically or physiologically dependent, such as tobacco smoking, overeating or abuse of legal and illegal drugs such as alcohol, marijuana and cocaine.

The apparatus is also useful for controlling dermatological discomfort like itching arising from external skin toxins such as poison ivy or internal or allergenic causes.

The apparatus is also useful in alleviating discomfort and pain arising from infections and injuries.

I believe that the application to the body of electrical impulses at certain rates and intensities from my device achieves these effects through increased production of the neuro-chemical endorphin.

To achieve these effects, I employ a two channel electrical stimulator having a pulse type output having two independent pulsing high voltage generators with independent intensity, duration and frequency controls. The electricity is applied to the skin through conducting electrodes held in place either with tape or with a spring-type headband. The high voltage in each circuit is generated by a multi-vibrator running at about 5,000 hertz driving a second multi-vibrator employed for amplification and pulse shaping and a power output transistor cyclically allowing and stopping current flow to the primary of a step up transformer, thereby inducing a series resonance whereby the induced oscillation causes a high output voltage to appear on the secondary side of the step up transformer where it is rectified and filtered.

The pulse frequency and duration are determined and controlled by the use of multi-vibrators which are used to control power transistor in the high voltage circuit which allows and prevents the flow of the DC high voltage through its associated electrodes.

DETAILED DESCRIPTION OF THE INVENTION

Figure 1:
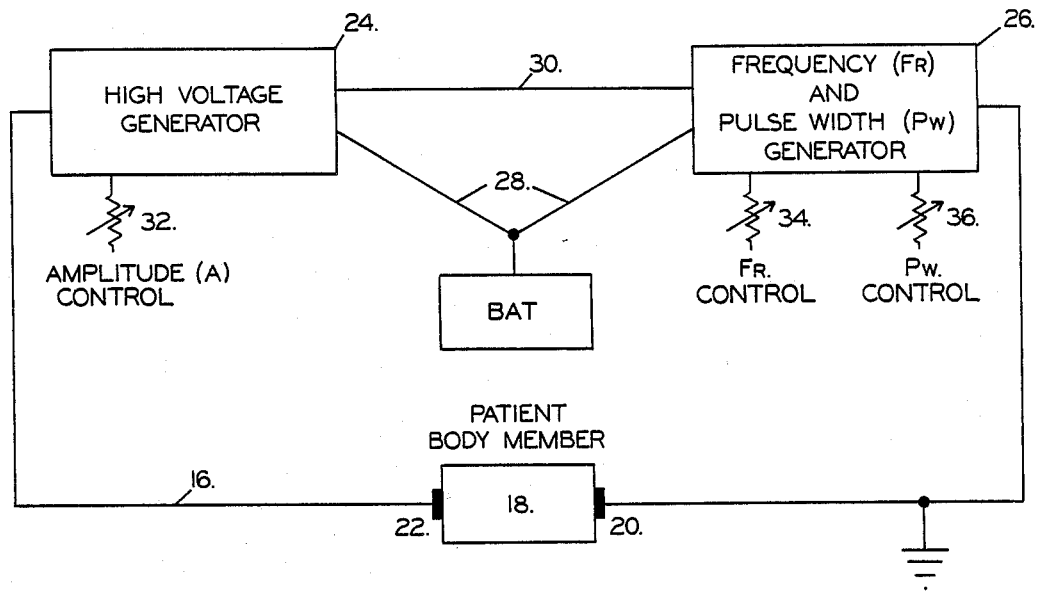
FIG. 1 shows a high voltage generator with manual amplitude control delivering its output to a frequency and pulse width generator with controls for these two variables and means for applying the output to a body member.

In FIG. 1, 24 is a high voltage generator having an amplitude control 32 to control the voltage of the output. The DC output of the high voltage generator is directed through a frequency and pulse width generator 26, having a frequency control 34 and a pulse width control 36. The high voltage output as controlled by the frequency and pulse width generator 26 is applied to a body member 18 through electrodes 20 and 22. Typically, such electrical stimulation has been applied to arms and legs to facilitate the knitting of broken bones and to the nervous system of the head through electrodes applied in the mastoidal region. The application of electric pulses at various frequencies to the head have been reported to induce analgesia, euphoria and in particular, substantial alleviation of withdrawal symptoms following the withdrawal of various kinds of addictive drugs such as heroin, morphine, marijuana, cocaine, amphetamines, tobacco and alcohol. The negative electrode is generally connected in the first trial behind the left ear and the positive behind the right. Initially, a frequency of 300 hertz will be employed with a ten percent pulse width under physician's control. The patient accessible amplitude control is intented to be adjusted up to the point where the patient observes a distinct tingling sensation and then backed off or reduced until the sensation just disappears.

If after a trial period the patient reports inadequate reduction in withdrawal symptoms, the physician will try reverse polarity if the patient is left-handed and/or increase the pulse frequency from 300 to 1,000.

Figure 2:
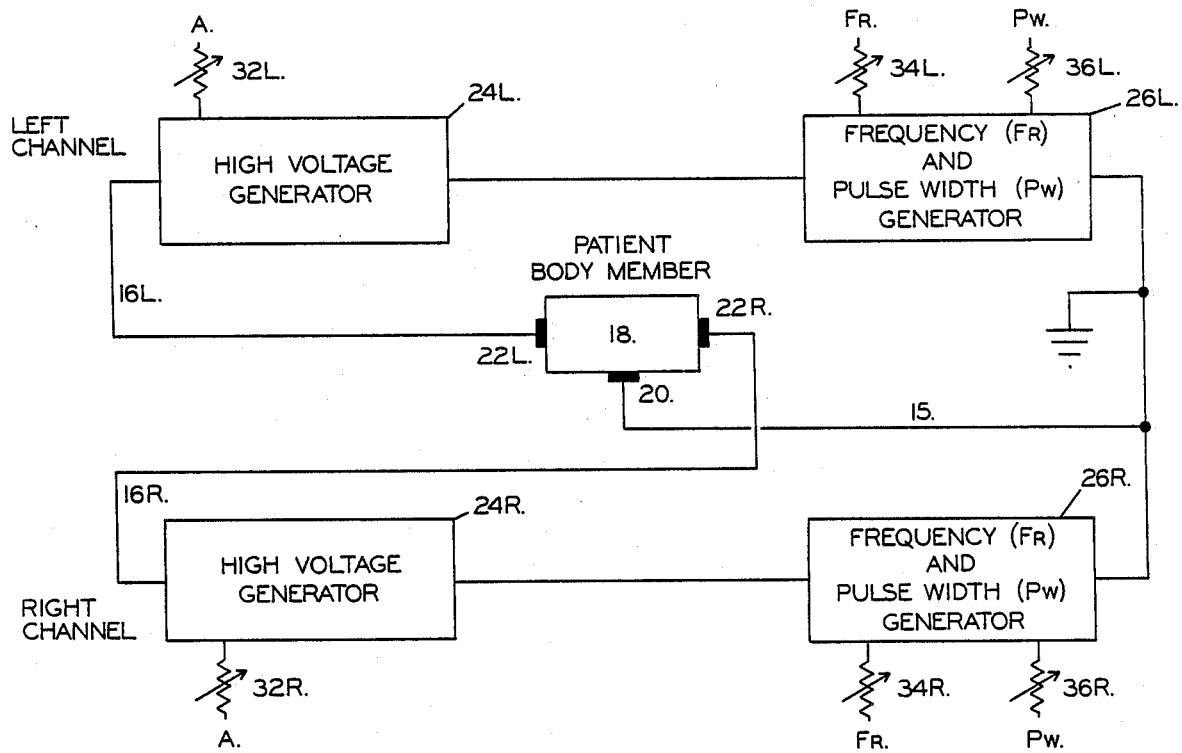
FIG. 2 shows a right channel and a left channel, each channel comprising a high voltage DC generator with control and a frequency pulse width generator with controls for each of those parmeters and wires and electrodes for applying the outputs to a body member.

FIG. 2 shows left channel and right channel pulsing assemblies each having substantially identical pulsing high voltage generators with similar components having the same numeral designations with R & L suffixes for right and left channel identification.

Each channel has a high voltage generator 24 with amplitude or voltage control 32 and a frequency and pulse width generator 26 having a frequency control 34 and a pulse width control 36. The lowest potential or grounded leads are commoned as wire 15 is connected to body electrode 20. The high voltage generators have output leads 26 connected to right and left electrodes 22R and 22L respectively. Common electrode 20 is most frequently positioned on the inner side of one upper arm with an elastic band holding the common electrode 20 in place. Typically, I have adjusted the right hand channel to a frequency of 300 hertz and ten percent pulse width and the left hand channel to a frequency of 50 to 70 hertz and five to ten percent pulse width, though the pulser is capable of frequencies from 1 hertz to 10,000 hertz and pulse widths from 5 percent to 30 percent.

I have found that patients treated during their withdrawal phase by the two channel pulser have decidedly fewer withdrawal symptoms; while those patients who, with the single channel device, have failed to persist in withdrawal and have resumed the use of their habit-forming chemical have, on a second try with the two channel device, frequently succeeded in totally eliminating their use of their chemical of addiction.

Figure 3:
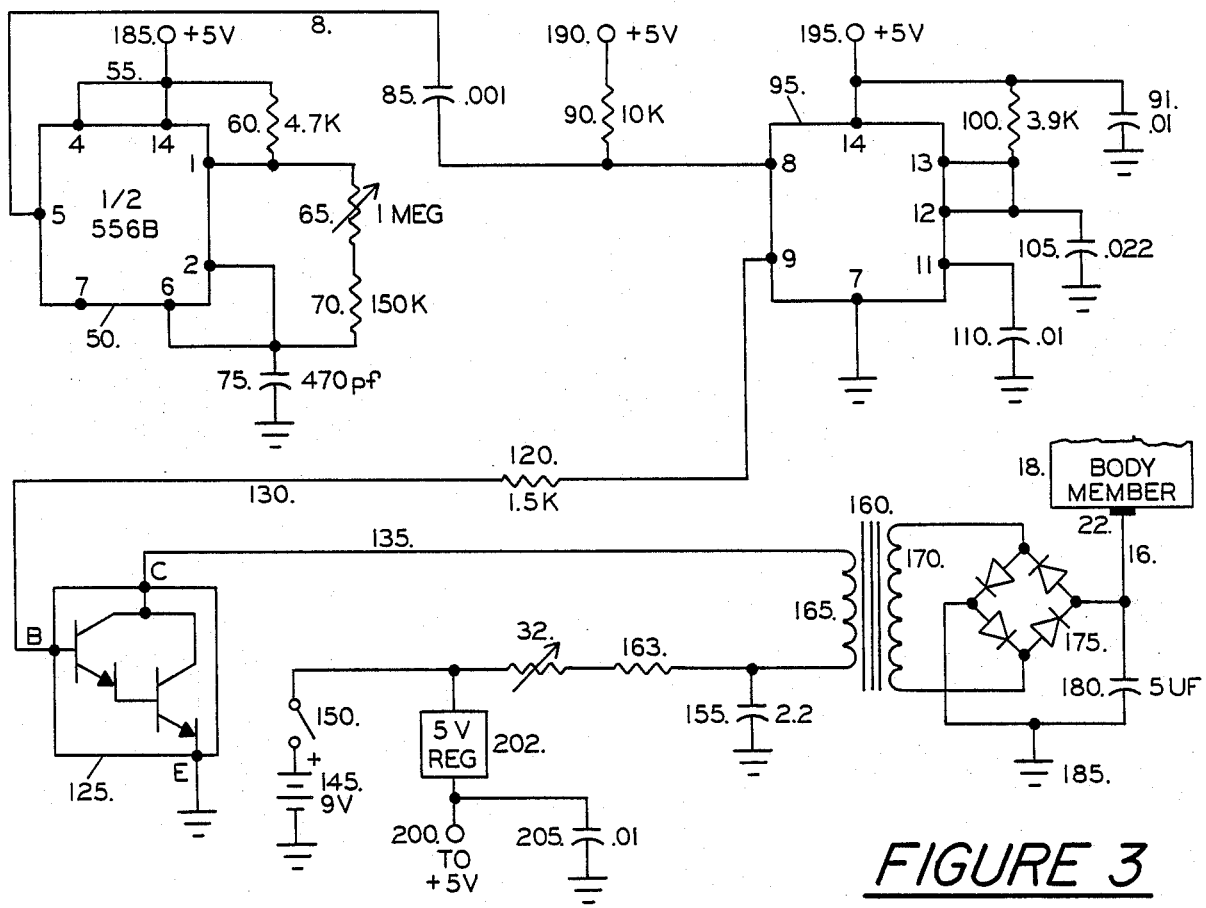
FIG. 3 shows typical circuitry employed for achieving the high voltage.

FIG. 3 is a schematic circuit diagram corresponding to the high voltage generator 24 of FIGS. 1 and 2.

Figure 4:
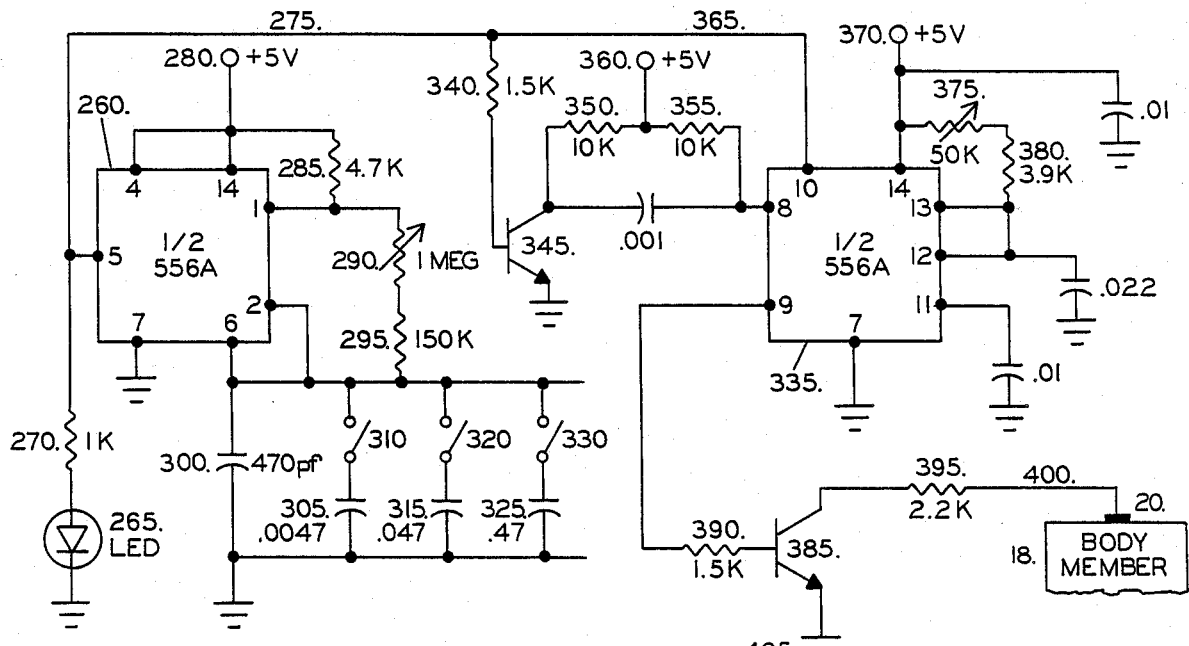
FIG. 4 shows typical circuitry for frequency and pulse width control in one channel only.

FIG. 4 is a schematic diagram of the frequency and pulse width generator 26 which controls the flow of high voltage electricity from the high voltage generator through the body member. Though appearing as separate circuit diagrams, the circuits of FIGS. 3 and 4 are linked together through the following common elements: ground, the body part under treatment and the connections between the 5 volt regulated power supply 202 of FIG. 3 whose output is supplied to the three 5 volt inputs 185, 190 and 195 in FIG. 3 and the three 5 volt inputs 280, 360 and 370 of FIG. 4.

In FIG. 3, the integrated circuits 50 and 95 are each one-half of an assembly in free running multi-vibrator mode. Potentiometer 65 is an internal adjustment used to adjust the multi-vibrator frequency which typically is 5,000 hertz. The square wave output of the multi-vibrator 50 is transmitted through line 8 and capacitor 85 to multi-vibrator 95 which amplifies and narrows the pulse width. The output of multi-vibrator 95 is by way of resistor 120 and wire 130 to power transistor 125.

When power switch 150 is closed by the user after body electrodes 22 and 20 are in place, power is supplied to the 5 volt regulator which thereupon supplies a 5 volt regulated source to 185, 190 and 195, the power inputs to the pulser circuitry for the high voltage generator. Closing power switch 150 also causes a pulsed flow of electricity through step up transformer primary 165. The intensity of this pulsed flow is controlled by potentiometer 32 which is under user control. The range of output voltage is 10 to 100.

The pulsing of the current flow through transformer primary 165 is controlled by power transistor 125 which, in turn is controlled by the pulsed output of multi-vibrator 95.

Capacitor 155 forms a series resonant circuit with transformer primary 165 substantially the same as in an automotive ignition circuit. When power transistor 125 allows current to flow through transformer primary 165 during the null portion between pulses output by multi-vibrator 95, a magnetic field containing stored energy is built up around transformer primary 165. When the direct current flow from battery 145 to ground through transformer primary 165 is abruptly terminated by cut-off of transistor 125, the energy stored in the transformer by the magnetic field around transformer primary 165 charges capacitor 155 as the magnetic field collapses, thereby inducing a high frequency alternating current electrical flow between capacitor 155 and transformer primary 165. This high frequency alternating current induces in the high voltage secondary 170 of the transformer 160 a high voltage alternating current output. This high voltage AC output is rectified to direct current by bridge rectifier 175 and filtered by filter capacitor 180 to a high voltage direct current output which is transmitted to the body member by way of wire 16 and electrode 22. It should be noted that the frequency of operation of multi-vibrator 50 and 95 have no effect on the frequency of the pulses applied to the body member since these pulses of 50 and 95 are rectified to direct current and pulse residuals are filtered out by a filter capacitor 180.

Power is supplied to the circuits of FIG. 4 from the regulated 5 volt power supply 202 of FIG. 3. In FIG. 4, multi-vibrator 260 has an operating rate controlled by switches 310, 320 and 330 with all switches open and only the 470 Pico-farad capacitor 300 in position, the output frequency is between 1,000 and 10,000 hertz as determined by the position of potentiometer 290. Closing switch 310 lowers the frequency range to between 100 and 1,000. Closing 320, in addition, lowers the frequency range to between 10 and 100. Closing switch 300 lowers the frequency rate to between 1 and 10 with intermediate values all achieved by adjustment of potentiometer 290. The output of multi-vibrator 260 is transmitted by a wire 275 through a shaping network to multi-vibrator 335. Multi-vibrator 335 provides control over the available pulse width range of 5 to 30 percent through the adjustment of potentiometer 375. The output of multivibrator 335 is through wire 388 to power transistor 385. This transistor 385 acts to allow and prevent the flow of high voltage electricity from the circuit of FIG. 3, depending on whether the pulse condition at transistor 385 allows or prevents current flow through it.

Figure 5:
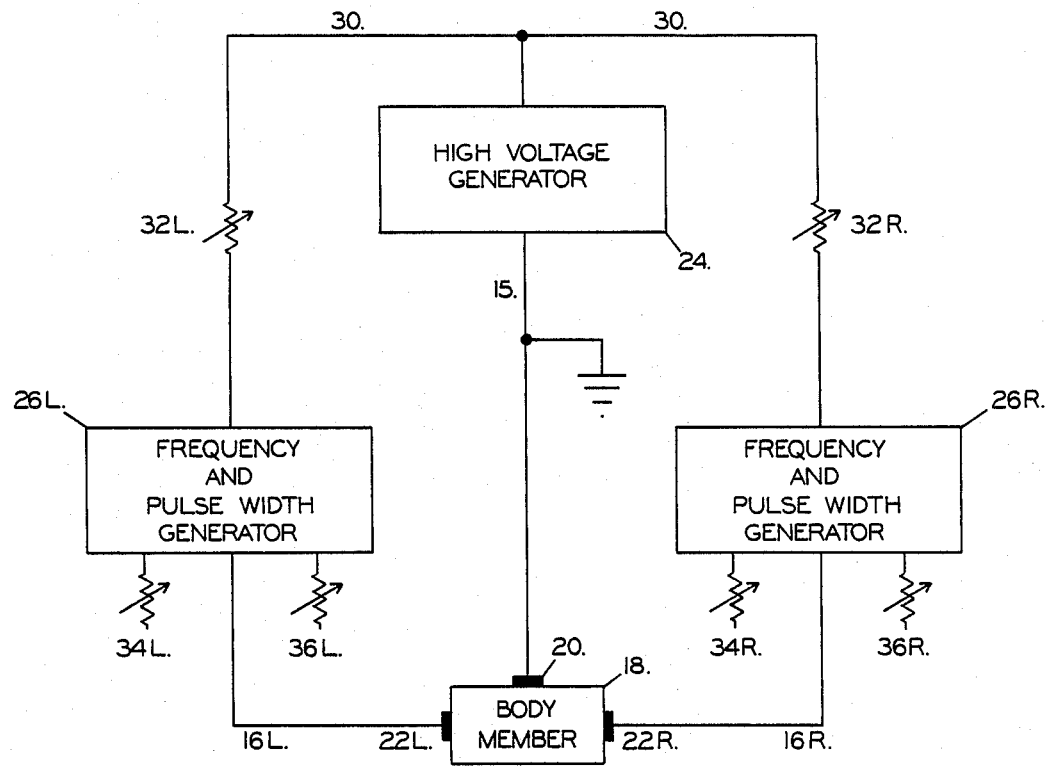
FIG. 5 shows a dual channel device having a single high voltage generator.

FIG. 5 shows a dual channel device utilizing a single high voltage generator 24 which distributes its high voltage energy to a left pulser 26L and a right pulser 26R by way of conductors 30. The conductor 30 supplying power to the right pulse has intensity control 32R. The conductor supplying power to the left pulser has independent intensity control 32L. The right and left channel pulses have independent frequency controls 34R and 34L and independent pulse width controls 36R and 36L. The body member 18 receives the high voltage pulses through conductors 16R and 16L and electrodes 22R and 22L respectively. The common electrode 20 completes the circuit to the high voltage generator and ground through conductor 15.

I claim:

1. Two channel means for applying electrical impulses to a body through electrodes comprising:
   a. a first circuit including a first electrode and a common electrode;

b. a second circuit including a second electrode and said common electrode;

and manual means in each circuit for independently controlling the frequency of pulses delivered to the first and second electrodes.

2. Means as in claim 1 which further includes means in each circuit for independently controlling the width of the pulses.

3. Means as in claim 1 which includes means for controlling the amplitude of the pulses.

4. The method of controlling human pain and discomfort including but not limited to that arising from withdrawal of a habituated chemical or activity comprising the steps of:

a. applying high voltage pulses to a body member between a first location and a common location at a first frequency and simultaneously b. applying high voltage pulses to the body member between a second location and said common location at a second frequency.

* * * * *